United States Patent [19]

Kempe et al.

[11] 4,278,801
[45] Jul. 14, 1981

[54] PREPARATION OF 5-HYDROXYMETHYLIMIDAZOLES

[75] Inventors: Uwe Kempe, Limburgerhof; Toni Dockner, Meckenheim; Anton Frank; Helmut Karn, both of Ludwigshafen, all of Fed. Rep. of Germany

[73] Assignee: BASF Aktiengesellschaft, Fed. Rep. of Germany

[21] Appl. No.: 119,959

[22] Filed: Feb. 8, 1980

[30] Foreign Application Priority Data

Mar. 2, 1979 [DE] Fed. Rep. of Germany ....... 2908212

[51] Int. Cl.$^3$ .......................................... C07D 233/64
[52] U.S. Cl. .................................... 548/342; 548/335; 548/346
[58] Field of Search ........................................ 548/342

[56] References Cited

FOREIGN PATENT DOCUMENTS

| 2637670 | 3/1977 | Fed. Rep. of Germany . |
| 2659851 | 11/1977 | Fed. Rep. of Germany . |
| 2800148 | 7/1979 | Fed. Rep. of Germany . |
| 2825547 | 12/1979 | Fed. Rep. of Germany . |
| 3052 | 7/1979 | European Pat. Off. . |
| 4534 | 10/1979 | European Pat. Off. . |

OTHER PUBLICATIONS

Mathieu, J., et al., Formation of C—C Bonds, Georg Thieme, Stuttgart, 1973, pp. 4–10.
Ewins, J. Chem. Soc., 99, 2055 (1911).
Durant, G., et al., J. Med. Chem., 19, 923–928, (1976).
Chemical Abstracts, 82: 43347d (1975), [Masui et al., Chem. Pharm. Bull. 22, 2359 (1974)].
Chemical Abstracts, 78: 58317k, (1973), [Godefrol et al., Rec. Trav. Chim., 91, 1383, (1972)].
Gordon, A., et al., The Chemist's Companion, John Wiley, New York, 1972, p. 77.
Chemic 7: 1871 (1913), [Wellisch, J., Biochem. 2, 49, 173–194 (1913)].

Primary Examiner—Richard A. Schwartz
Attorney, Agent, or Firm—Keil & Witherspoon

[57] ABSTRACT

A process for the manufacture of 5-hydroxymethylimidazoles by reaction of an imidazole with formaldehyde or an oligomer of formaldehyde in aqueous hydrochloric acid solution containing from 5 to 18% by weight of hydrogen chloride, at from 80° to 160° C., if desired in a closed system under pressure, followed by isolation in the form of its hydrochloride of the 5-hydroxymethylimidazole obtained.

4 Claims, No Drawings

PREPARATION OF 5-HYDROXYMETHYLIMIDAZOLES

The present invention relates to a process for the preparation of 5-hydroxymethylimidazoles in the form of their hydrochlorides, by hydroxymethylation in aqueous hydrochloric acid solution.

The chloromethylation of aromatic compounds by reaction with formaldehyde in the presence of concentrated hydrochloric acid, and in the presence or absence of a catalyst, for example zinc chloride or aluminum chloride, is a well-known reaction. The base-catalyzed condensation of reactive aromatics, eg. phenol, pyrrole, indole, quinoline and their derivatives, with formaldehyde, to give hydroxymethyl compounds, is also extensively described in the literature (J. Mathieu and J. Weill-Raynal, Formation of C—C-Bonds, pages 4–10 and 29–31, Georg-Thieme-Verlag (1973)). On the other hand, the hydroxymethylation of aromatics, especially of imidazole, in the presence of hydrochloric acid has not been disclosed.

Thus, for example, the preparation of 4-substituted 5-hydroxymethylimidazoles has only been described for the case of 4-methyl-5-hydroxymethylimidazole, obtained by reaction of 4-methylimidazole with formaldehyde (J. Chem. Soc. 99 (1911), 2,055).

Disadvantages of this process are the low yields, the low selectivity and the fact that the crude product is worked up using picric acid, so that it is difficult to obtain the pure 5-hydroxymethyl compound. Because of the difficulty of preparing such compounds by this method, German Laid-Open Application DOS No. 2,637,670 prepares 4-methyl-5-hydroxymethylimidazole from 4-methyl-5-carboxylic acid esters by reduction with alkali metals or calcium in liquid ammonia. This process is laborious and difficult to carry out on an industrial scale because liquid ammonia and alkali metals are used. The preparation of 4-methyl-5-hydroxymethylimidazole by reducing a corresponding carboxylic acid ester with lithium aluminum hydride (J. Med. Chem. 19 (1976), 923–928) is equally involved and even more expensive.

German Patent Application No. P 28 00 148 proposes the preparation of 4-methyl-5-hydroxymethylimidazole in the form of its hydrochloride, by hydrolysis of 4-methyl-5-chloromethylimidazole, namely by heating 4-methyl-5-chloromethylimidazole hydrochloride in aqueous solution at 50°–60° C. In a prior separate reaction step, 4-methyl-5-chloromethylimidazole hydrochloride is prepared by heating formaldehyde and 4-methylimidazole in concentrated aqueous hydrochloric acid solution.

Further, German Patent Application No. P 28 25 547.2 proposes the preparation of 5-hydroxymethylimidazoles from the corresponding 1-hydroxymethylimidazoles by rearrangement in aqueous hydrochloric acid. The 1-hydroxymethylimidazoles themselves are prepared by reacting the imidazole with paraformaldehyde or trioxane, advantageously in the presence of an aromatic hydrocarbon, especially toluene.

It is an object of the present invention to prepare 5-hydroxymethylimidazoles in a very simple manner, and in a form free from by-products, on an industrial scale.

We have found, surprisingly, that this object is achieved and that 5-hydroxymethylimidazoles of the formula 1

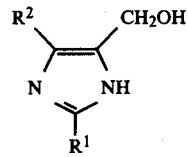

where $R^1$ is hydrogen or alkyl of 1 to 18 carbon atoms, or aryl or aralkyl, and $R^2$ is alkyl of 1 to 18 carbon atoms or aryl, can be prepared directly in a single-stage reaction, if an imidazole of the formla 2

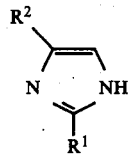

where $R^1$ and $R^2$ have the meanings given for formula 1, is reacted with formaldehyde or an oligomer of formaldehyde in aqueous hydrochloric acid solution, containing from 5 to 18% by weight of hydrogen chloride, based on the water present, at from 80° to 160° C., if appropriate in a closed system under pressure, and the resulting 5-hydroxymethylimidazole is then isolated in the form of its hydrochloride.

Aryl is in particular phenyl and aralkyl is in particular benzyl, β-phenylethyl or a higher homolog.

The process according to the invention is preferentially used to prepare 5-hydroxymethylimidazoles, where $R^1$ is hydrogen or alkyl of 1 to 4 carbon atoms and $R^2$ is alkyl of 1 to 4 carbon atoms.

The process according to the invention is preferentially carried out at from 100° to 140° C. If the reaction is carried out in a closed system, for example in an enamelled kettle or a corrosion-resistant metal autoclave, the autogenous pressure corresponding to the temperature used is set up.

The formaldehyde is used in the form of the conventional aqueous solution containing from 15 to 40% by weight of formaldehyde, or as a gas, or in the form of its oligomers, eg. paraformaldehyde or 1,3,5-trioxane. The molar ratio of imidazole to formaldehyde is advantageously from 1:1 to 1:1.5.

Within the stated concentration range of hydrogen chloride, the molar ratio of imidazole to hydrogen chloride is from 1:1.5 to 1:5. The presence of from 12 to 16% by weight of hydrogen chloride is preferred.

The reaction is as a rule complete after from 20 to 60 hours.

After completion of the reaction, the mixture can be worked up in the conventional manner by concentrating the aqueous hydrochloric acid solution at from 10° to 120° C., preferably from 30° to 45° C., and isolating the resulting hydrochloride by filtering off and then washing with acetone or methanol or another lower monohydric alcohol of 2 to 6 carbon atoms, the product then being dried.

A very particularly pure 5-hydroxymethylimidazole is obtained by bringing the pH of the reaction mixture to 7–12 by means of an alkali, preferably by means of 20–60% strength by weight sodium hydroxide solution, extracting the product with a water-immiscible organic extractant, advantageously butanol, pentanol or 2-ethylhexanol, and then reprecipitating the hydrochloride by introducing hydrogen chloride. Using this preferred method it is possible to use technical-grade 4-methylimidazole which is from 85 to 93% pure, since by-products of the starting material can only be separated from 4-methyl-5-hydroxymethylimidazole at great expense, due to the differences in solubility of the hydrochlorides in water being slight. In spite of the resulting 5-hydroxymethylimidazoles being extremely easily soluble in water, isolation by means of the solvents mentioned succeeds without difficulty.

Preferably, about 50–80% of the extractant are distilled off, before precipitation, at from 5° to 100° C., but especially at from 10° to 50° C.; the small amount of sodium chloride formed is filtered off and gaseous hydrogen chloride is introduced at from 5° to 45° C. If desired, the product can be recrystallized from a monohydric alcohol of 1 to 6 carbon atoms, for example methanol or isopropanol, which may contain up to 25% by volume of water.

Compared to the two-stage process referred to above, the process according to the invention is distinguished by the fact that it entails a one-stage reaction without the use of organic solvents, and gives the desired 5-hydroxymethylimidazole exclusively, and in high yields.

It would be expected by those skilled in the art that at the required reaction temperatures and reaction times a shift in equilibrium to the 5-chloromethyl compounds might occur. Interestingly, under the conditions according to the invention, in aqueous hydrochloric acid solutions containing from 5 to 18% by weight of hydrogen chloride, based on the water present, the hydroxymethylation takes place without formation of 5-chloromethyl compounds. It was not to be expected that pure 5-hydroxymethylimidazole would be formed exclusively, without side reactions and without contamination by chloromethyl compounds.

In addition to the compounds mentioned in the Examples, the following 5-hydroxymethylimidazoles, for example, are prepared in the same way: 2-phenyl-4-methyl-5-hydroxymethylimidazole, 2-isopropyl-4-methyl-5-hydroxymethylimidazole, 2-methyl-4-ethyl-5-hydroxymethylimidazole, 2-methyl-4-phenyl-5-hydroxymethylimidazole and 2-benzyl-4-methyl-5-hydroxymethylimidazole.

The Examples which follow illustrate, but do not limit, the process according to the invention. Parts by weight bear the same relation to parts by volume as the kilogram to the liter.

EXAMPLE 1

82 parts by weight of 98.7% pure 4-methylimidazole, 560 parts by volume of water, 450 parts by weight of about 37% strength by weight aqueous hydrochloric acid and 100 parts by weight of 30% strength by weight aqueous formaldehyde solution are refluxed for 48 hours at 120° C. in a closed vessel. After distilling off the water, 160 parts by weight of residue are obtained. This material is recrystallized from 400 parts by volume of ethanol. After drying under reduced pressure, 91 parts by weight of 4-methyl-5-hydroxymethylimidazole hydrochloride of melting point 225.2°–232.3° C. are obtained. The mother liquor, after concentration, gives a further 21 parts by weight of the same compound, and the residue from the mother liquor gives yet a further 5 parts by weight of the same compound.

The yield of crude product is 117 parts by weight (78.8% of theory).

EXAMPLE 2

The reaction is carried out as described in Example 1, the parts by weight being grams and the parts by volume milliliters, but after a reaction time of 48 hours at 120° C., the aqueous hydrochloric acid reaction solution is cooled to 20°–30° C. with ice and its pH is brought to 8.5, at this temperature, by means of 60% strength by weight sodium hydroxide solution. The solution obtained is extracted by shaking with three 1 liter portions of butanol and the combined butanol phase is concentrated to a volume of about 1 liter. When it has cooled, a slight precipitate of sodium chloride is filtered off and 40 g of hydrogen chloride are passed into the solution, which is kept at 20°–30° C. by cooling with ice. Thereafter, the solution is cooled to 10° C. and left to stand at this temperature for 2 hours. 83 g of 4-methyl-5-hydroxymethylimidazole hydrochloride of melting point 222°–231° C. are obtained. On concentrating the filtrate until it crystallizes, a further 17 g, of melting point 206°–229.5° C., are obtained. The residue from the mother liquor amounts to 30.5 g; by stirring this residue with 30 ml of i-propanol, a further 7 g of product, of melting point 192.3°–207.1° C., can be obtained. According to the NMR spectrum and examination by high pressure liquid chromatography, the samples are identical. The yield of crude product is therefore 107 g (72.1% of theory). 83 g of this product are recrystallized from 210 ml of aqueous n-propanol. 60 g of 4-methyl-5-hydroxymethylimidazole hydrochloride of melting point 230.5°–239° C. are obtained.

EXAMPLE 3

The reaction mixture used is as in Example 2, but is extracted by shaking with three 1 liter portions of ethylhexanol. After concentrating the extract and precipitating the product as described in Example 2, 60.5 g (40.7% of theory) of 4-methyl-5-hydroxymethylimidazole hydrochloride, of melting point 206.7°–214.5° C., are obtained.

EXAMPLE 4

The reaction mixture used is as in Example 2, but extraction is carried out with six 250 ml portions of pentanol. After concentrating the combined pentanol phase to 500 ml, the procedure described in Example 1 is followed. The yield of crude product is 79.5 g (53.5% of theory) of melting point 206.5°–214° C.

EXAMPLE 5

82 parts by weight of 99% pure 4-methylimidazole are introduced into a solution of 245 parts by volume of water and 225 parts by weight of about 36% strength by weight concentrated aqueous hydrochloric acid, and the mixture is refluxed with 105 parts by weight of about 30% strength by weight aqueous formaldehyde solution for 24 hours at 130° C. under the autogenous pressure.

The hydrochloric acid is neutralized with 150 parts by weight of about 60% strength by weight concentrated aqueous sodium hydroxide solution at 20°–30° C. internal temperature and the mixture is brought to a pH of 8.5. This solution is extracted four times with 500 parts by volume of n-butanol and the combined butanol extract is concentrated to 750 parts by volume under reduced pressure, at a bath temperature of 50°–60° C., and is then cooled. Sodium chloride which has precipitated is filtered off, and 40 parts by weight of gaseous hydrogen chloride are passed into the filtrate at 20°–30° C. The solution is cooled to 10° C. and the crystals which precipitate are filtered off and washed with a small amount of acetone. 95 parts by weight of 4-methyl-5-hydroxymethylimidazole hydrochloride are obtained. A further 14 parts by weight are obtained by concentrating the mother liquor.

The residue from the mother liquor, when fractionally crystallized twice with i-propanol, gives, respectively, a further 13 and 2 parts by weight of crystals identical with the first crop. The yield of crude 4-methyl-5-hydroxymethylimidazole hydrochloride is 124 parts by weight (83.5% of theory) of melting point 222°–229° C.

According to high pressure liquid chromatography and according to the nuclear magnetic resonance spectrum, the product consists of a single compound.

EXAMPLE 6

The procedure described in Example 1 is followed, except that 82 parts by weight of 93.3% pure 4-methylimidazole are employed. The aqueous hydrochloric acid solution is concentrated under reduced pressure at 35° to 40° C. internal temperature to give 168 parts by weight of a crystalline residue.

Variant A 84 parts by weight of the crystals are recrystallized from 350 parts by volume of butanol. After filtering off the product and drying it, 41 parts by weight of 4-methyl-5-hydroxymethylimidazole hydrochloride (59% of theory), of melting point 240°–245° C., are obtained.

Variant B 84 parts by weight of the crystals are stirred with 84 parts by volume of n-butanol at room temperature. The butanol is filtered off. 48.6 parts by weight (70% of theory) of 4-methyl-5-hydroxymethylimidazole hydrochloride, of melting point 240°–245° C., are obtained.

EXAMPLE 7

110 parts by weight of 2-ethyl-4-methylimidazole, 560 parts by volume of water, 450 parts by weight of about 36% strength concentrated hydrochloric acid and 100 parts by weight of 30% strength by weight aqueous formaldehyde solution are refluxed for 48 hours at about 1 bar and 120° C., and the batch is then concentrated under reduced pressure. After recrystallizing the residue from ethanol, 144.32 parts by weight (82% of theory) of 2-ethyl-4-methyl-5-hydroxymethylimidazole hydrochloride, of melting point 237°–238° C., are obtained.

EXAMPLE 8

103 parts by weight of 93.5% pure 4-ethylimidazole, 560 parts by volume of water, 450 parts by weight of aqueous concentrated hydrochloric acid of about 36% strength and 100 parts by volume of 30% strength by weight aqueous formaldehyde solution are heated for 48 hours at 120° C. under pressure (about 1 bar) and the batch is then concentrated under reduced pressure.

193 parts by weight of a partially crystalline residue are obtained. For purification, the residue is dissolved in hot isopropanol and 130.4 parts by weight (80% of theory) of 4-ethyl-5-hydroxymethylimidazole hydrochloride, of melting point 135°–137° C., are precipitated by adding acetone at room temperature.

We claim:

1. A process for the preparation of a 5-hydroxymethylimidazole of the formula 1

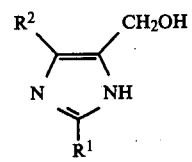

where $R^1$ is hydrogen or alkyl of 1 to 18 carbon atoms, phenyl, benzyl or β-phenylethyl, and $R^2$ is alkyl of 1 to 18 carbon atoms or phenyl, wherein an imidazole of the formula 2

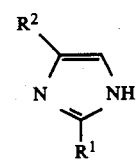

where $R^1$ and $R^2$ have the meanings given for formula 1, is reacted with formaldehyde or an oligomer of formaldehyde is aqueous hydrochloric acid solution, containing from 5 to 18% by weight of hydrogen chloride, at from 80° to 160° C., if appropriate in a closed system under pressure, and the resulting 5-hydroxymethylimidazole is isolated in the form of its hydrochloride, the ratio of imidazole to hydrogen chloride being from 1:1.5 to 1:5.

2. A process as claimed in claim 1, wherein the molar ratio of imidazole to formaldehyde is from 1:1 to 1:1.5.

3. A process as claimed in claim 1 or 2, wherein, after completion of the reaction, the pH of the reaction mixture is brought to 7–12 by means of a base, and the 5-hydroxymethylimidazole is then extracted with a water-immiscible organic solvent and is reprecipitated as the hydrochloride from the organic solvent by introducing hydrogen chloride.

4. A process as claimed in claims 1 or 2, wherein $R^1$ is hydrogen or alkyl of 1 to 4 carbon atoms and $R^2$ is alkyl of 1 to 4 carbon atoms.

* * * * *